United States Patent
Abate et al.

(10) Patent No.: US 10,232,373 B2
(45) Date of Patent: Mar. 19, 2019

(54) SIZE ALTERNATING INJECTION INTO DROPS TO FACILITATE SORTING

(71) Applicant: GNUBIO, INC., Cambridge, MA (US)

(72) Inventors: Adam R. Abate, San Francisco, CA (US); Sepehr Kiani, Watertown, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 70 days.

(21) Appl. No.: 15/316,128

(22) PCT Filed: Jun. 16, 2015

(86) PCT No.: PCT/US2015/036080
§ 371 (c)(1),
(2) Date: Dec. 2, 2016

(87) PCT Pub. No.: WO2015/195698
PCT Pub. Date: Dec. 23, 2015

(65) Prior Publication Data
US 2017/0128942 A1    May 11, 2017

Related U.S. Application Data

(60) Provisional application No. 62/012,516, filed on Jun. 16, 2014.

(51) Int. Cl.
*B01L 3/00* (2006.01)
*G01N 15/10* (2006.01)
(Continued)

(52) U.S. Cl.
CPC ....... *B01L 3/502784* (2013.01); *B01L 3/0241* (2013.01); *B01L 3/5027* (2013.01);
(Continued)

(58) Field of Classification Search
CPC .............. B01F 13/0071; B01F 13/0076; B01F 13/0062; B01F 13/0074; B01F 3/0807;
(Continued)

(56) References Cited

U.S. PATENT DOCUMENTS

2006/0210443 A1\* 9/2006 Stearns ................. B01L 3/0268
422/400
2007/0003442 A1   1/2007 Link et al.
(Continued)

FOREIGN PATENT DOCUMENTS

CN    101765762 A    6/2010
CN    103765068 A    4/2014
(Continued)

OTHER PUBLICATIONS

International Search Report and Written Opinion dated Jun. 16, 2015 in PCT/US15/36080, 12 pages.
(Continued)

*Primary Examiner* — Jennifer Wecker
(74) *Attorney, Agent, or Firm* — Kilpatrick Townsend and Stockton LLP

(57) ABSTRACT

This invention pertains to a new microfluidic device and the method of using it to sort droplets. The method comprises (a) providing a plurality of droplets flowing in a microfluidic channel, wherein the plurality of droplets comprise desired droplets and undesired droplet (b) identifying desired droplets in the plurality of droplets, (c) changing volume of the desired droplets relative to volume of the undesired droplets such that at least some of the desired droplets have a different volume than the undesired droplets, and (d) passively sorting the desired droplets having the different volume from the undesired droplets.

23 Claims, 6 Drawing Sheets

(51) Int. Cl.
*G01N 15/14* (2006.01)
*B01L 3/02* (2006.01)
*C12M 3/06* (2006.01)
*C12M 1/00* (2006.01)
*C12Q 1/6806* (2018.01)
*C12Q 1/68* (2018.01)
*G01N 15/02* (2006.01)
*G01N 35/10* (2006.01)
*G01N 27/447* (2006.01)

(52) U.S. Cl.
CPC ............ *C12M 23/16* (2013.01); *C12M 47/04* (2013.01); *C12Q 1/6806* (2013.01); *G01N 15/10* (2013.01); *G01N 15/14* (2013.01); *B01L 3/502746* (2013.01); *B01L 3/502761* (2013.01); *B01L 3/502776* (2013.01); *B01L 3/502792* (2013.01); *B01L 2200/0652* (2013.01); *B01L 2300/0654* (2013.01); *B01L 2300/0816* (2013.01); *B01L 2300/0864* (2013.01); *B01L 2300/0867* (2013.01); *B01L 2300/0883* (2013.01); *B01L 2400/043* (2013.01); *B01L 2400/0409* (2013.01); *B01L 2400/0424* (2013.01); *B01L 2400/0433* (2013.01); *B01L 2400/0436* (2013.01); *B01L 2400/0439* (2013.01); *B01L 2400/0442* (2013.01); *B01L 2400/0454* (2013.01); *B01L 2400/0487* (2013.01); *B01L 2400/0622* (2013.01); *B01L 2400/084* (2013.01); *G01N 15/0255* (2013.01); *G01N 27/44791* (2013.01); *G01N 2015/0288* (2013.01); *G01N 2015/1006* (2013.01); *G01N 2015/1081* (2013.01); *G01N 2035/1034* (2013.01)

(58) Field of Classification Search
CPC .... B01F 5/0256; B01F 5/0471; B01F 5/0646; B01F 5/0655; B01F 5/0682; B01F 5/0689; B01L 2300/0867; B01L 3/502784; B01L 2300/0816; B01L 3/5027; B01L 2200/0652; B01L 2200/0673; B01L 2300/0864; B01L 2300/1861; B01L 2400/0415; B01L 2400/0424; B01L 2400/0436; B01L 2400/0442; B01L 2400/0487; B01L 2200/14; B01L 2300/0883; B01L 2400/0409; B01L 2400/043; B01L 2400/0433; B01L 2400/0439; B01L 2400/0454; B01L 2400/0622; B01L 2400/084; B01L 3/0268; B01L 3/50273; B01L 3/502746; B01L 3/502761; B01L 3/502776; B01L 3/502792; B01L 2300/0654; B01L 3/0241; F16K 99/0019; F16K 99/0042; F16K 99/0051; C12M 23/16; C12M 41/36; C12M 47/04; G01N 15/0255; G01N 15/10; G01N 15/14; G01N 2015/0288; G01N 2015/1006; G01N 2015/1081; G01N 2035/1034; G01N 27/44791; C12Q 1/6806
See application file for complete search history.

(56) References Cited

U.S. PATENT DOCUMENTS

| | | | |
|---|---|---|---|
| 2007/0007220 A1* | 1/2007 | Takagi | B01D 43/00 210/800 |
| 2008/0053205 A1 | 3/2008 | Pollack et al. | |
| 2008/0074449 A1 | 3/2008 | Lee et al. | |
| 2012/0132288 A1* | 5/2012 | Weitz | B01F 5/0471 137/13 |
| 2013/0011210 A1* | 1/2013 | Toner | B01D 21/0087 406/86 |
| 2013/0225418 A1 | 8/2013 | Watson | |
| 2016/0136643 A1* | 5/2016 | Larson | B01L 3/502715 506/2 |

FOREIGN PATENT DOCUMENTS

| | | |
|---|---|---|
| WO | 2008/130977 A2 | 10/2008 |
| WO | 2012/135259 A1 | 10/2012 |

OTHER PUBLICATIONS

Extended European Search Report dated Nov. 29, 2017 in EP Application 15809718.8; 12 pages.

\* cited by examiner

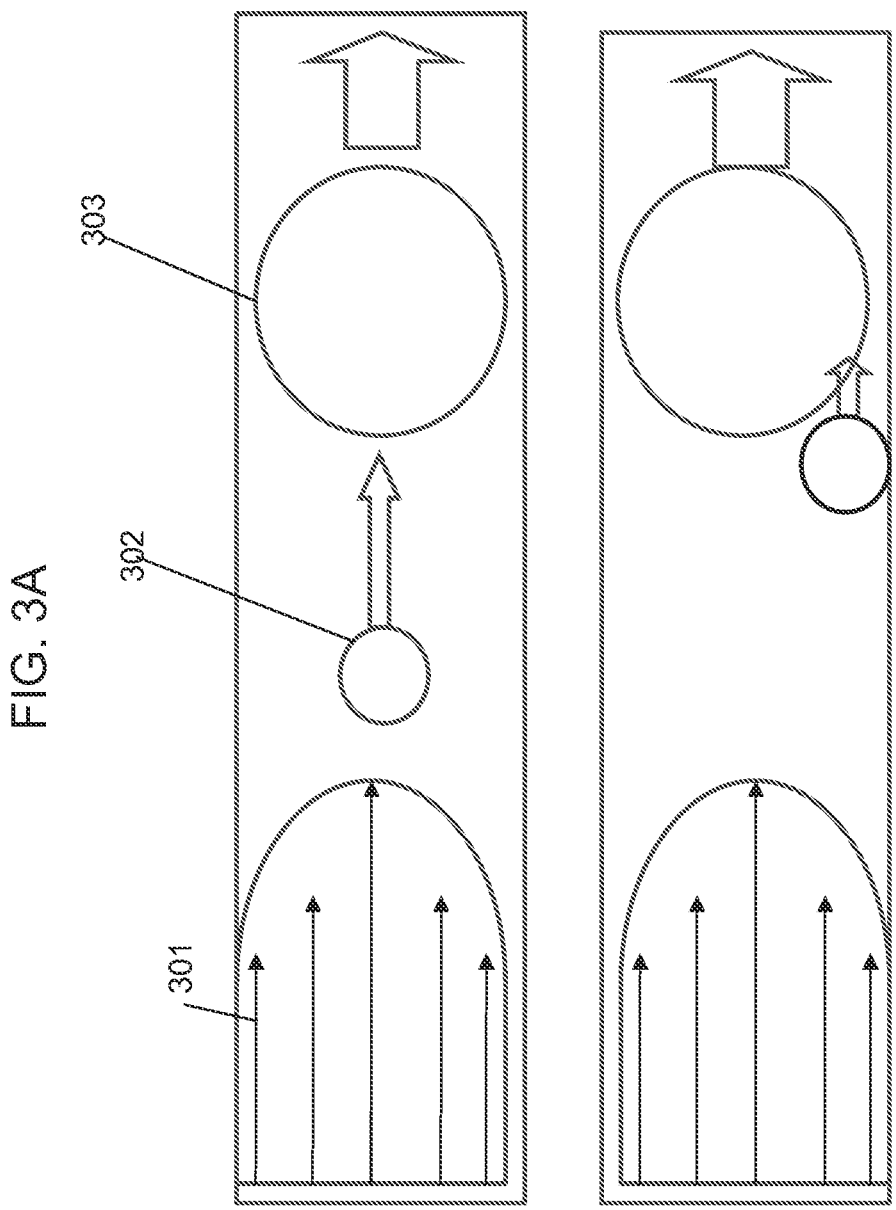

SIZE ALTERNATING INJECTION INTO DROPS TO FACILITATE SORTING

CROSS-REFERENCE TO RELATED PATENT APPLICATIONS

The present application is the U.S. National Stage entry of PCT/US2015/036080, filed Jun. 16, 2015 which claims benefit of priority to U.S. Provisional Patent Application No. 62/012,516, filed Jun. 16, 2014, which is incorporated by reference for all purposes.

FIELD OF THE INVENTION

The present invention is in the technical field of microfluidics. More particularly, the present invention relates to a microfluidic device for changing droplet volume of certain droplets and then passively sorting the resulting droplets, e.g., based on volume.

BACKGROUND OF THE INVENTION

Sorting is a function that must be performed in many droplet-based microfluidic biological applications. For example, when performing a cellular screen, cells having the desirable trait must be extracted from the full population of cells by droplet sorting. In the example of sequencing DNA, drops containing undesirable products, or lacking the target DNA, must be removed by sorting, so that they are not processed in the steps that follow. Droplet sorting can be achieved using a variety of methods. For example, using single layer membrane valves or by pressuring bifurcating channel geometry, droplets can be sorted into different channels. Alternatively, by using dielectrophoretic forces or surface acoustic waves, droplets can be sorted at much higher speeds.

BRIEF SUMMARY OF THE INVENTION

This invention pertains to a new microfluidic device and the method of using the device to sort droplets.

In some embodiments, a method to sort desired droplets from undesired droplets is provided. In some embodiments, the method comprises (a) providing a plurality of droplets flowing in a microfluidic channel, wherein the plurality of droplets comprise desired droplets and undesired droplets, (b) identifying desired droplets in the plurality of droplets, (c) changing volume of the desired droplets relative to volume of the undesired droplets such that at least some of the desired droplets have a different volume than the undesired droplets, and (d) passively sorting the desired droplets having the different volume from the undesired droplets, thereby separating the desired droplets from undesired droplets In some embodiments, the identifying comprises identifying the desired droplets with an optical detector.

In some embodiments, the changing comprises selectively injecting or removing fluid from the desired droplets. In some embodiments, a volume controller increases the volume of the desired droplets in response to an electrical field. In some embodiments, a volume controller decreases the volume of the desired droplets in response to an electrical field. In some embodiments, the changing comprises selectively injecting or removing fluid from the undesired droplets. In some embodiments, a volume controller increases the volume of the undesired droplets in response to an electrical field. In some embodiments, a volume controller decreases the volume of the undesired droplets in response to an electrical field. In some embodiments, the changing results in at least a majority of the desired droplets in the plurality of droplets having a different volume than the undesired droplets.

In some embodiments, the passively sorting comprises forcing droplets towards a wall of the microfluidic channel, wherein droplets of different sizes are forced a different distance towards the wall. In some embodiments, the forcing comprises adding a phase fluid continuously to the microfluidic channel through an intersecting channel to push the droplets toward the wall. In some embodiments, the forcing comprises applying a deflection electrical field to the microfluidic channel to force the droplets towards the wall.

In some embodiments, the changing volume of the desired droplets relative to the volume of the undesired droplets further comprises injecting a reagent that changes the electromagnetic properties of the droplets to increase deflection distance differentiation among the droplets of different volume caused by the deflection electric field.

In some embodiments, the passive sorting is performed by a method selected from the group consisting of dielectrophoresis, obstacle induced separation, deformability selective separation, inertial migration, and inertial Dean flow.

Also provided are systems for sorting droplets. In some embodiments, the system comprises a source of droplets in fluid communication with a microfluidic channel, an optical detector positioned for determination of desired droplets in a plurality of droplets in the microfluidic channel, a droplet volume controller, downstream of the optical detector, to change the volume of the desired droplets, and a droplet size sorter, downstream of the droplet volume controller, in fluid communication with the channel, which separates the desired droplets from undesired droplets.

In some embodiments, the volume controller injects fluid into desired droplets to increase the volume of the droplets. In some embodiments, the volume controller comprises an electrical field generator such that the volume controller injects fluid into desired droplets in response to an electrical field.

In some embodiments, the volume controller reduces the volume of the desired droplets. In some embodiments, the volume controller comprises an electrical field generator such that the volume controller reduces the volume of the desired droplets in response to an electrical field.

In some embodiments, the microfluidic channel further comprises an intersecting channel for providing a phase fluid that is added to the microfluidic channel to size-differentially force the droplets toward a wall of the microfluidic channel.

In some embodiments, the system further comprises one or more electrodes for generating a deflection electrical field applied to the microfluidic channel to deflect the droplets within the microfluidic channel, which results in deflection distances that correspond to the volume of the droplets and allows desired droplets to be separated from the undesired droplets while passing through the size sorter.

In some embodiments, the volume controller additionally injects a reagent that changes the electromagnetic properties of the droplets to increase deflection distance differentiation among the droplets of different volume caused by the deflection electric field.

In some embodiments, the droplet size sorter is selected from the group consisting of a dielectrophoresis droplet size sorter, an obstacle induced separation droplet size sorter, a deformability selective separation droplet size sorter, an inertial migration droplet size sorter, and an inertial Dean flow droplet size sorter.

Additional embodiments are described elsewhere herein.

BRIEF DESCRIPTION OF THE DRAWINGS

FIG. 3A and 3B illustrates an aspect in which different droplets of different size flow differently in a microchannel and are passively sorted. The arrows (301) at the left indicate speed of flow within the microchannel. As depicted, the flow profiles are parabolic in the channel. The fastest flows are in the center of the channel and they drop off to the edge of the channel where at the boundary with the wall, the flow is zero or nearly zero. In some embodiments, drops flow one-by-one in a channel, where their position is centered, and evenly spaced out between neighboring drops. A large drop that fills almost the entire channel (e.g., 302, 304) will sample the entire flow profile across the parabola, while a smaller drop (303, 305) will sample only the faster flows in the center of the channel. The large drop (302, 304) will move slower than the small one (303, 305). The small drop (303, 305) catches up to the large drop (302, 304), unable to pass as the size of the channel is too small to squeeze through and thus the small drop (303) is pushed closer to the side of the channel. When these drops meet a bifurcation, such as depicted in FIG. 3B, because the smaller drop (305) is closer to the wall of the channel, it will naturally follow those streamlines on the edges.

DETAILED DESCRIPTION OF THE INVENTION

Figure 1:
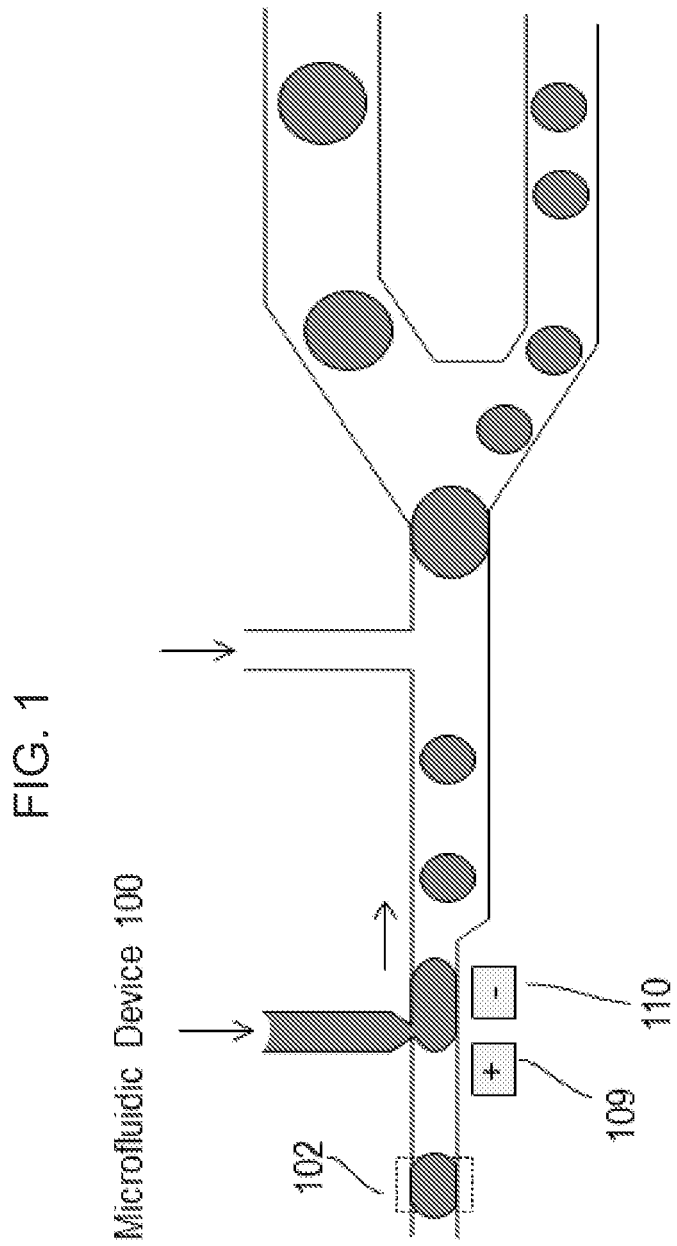
FIG. 1 provides a schematic illustration of a system for detecting desired droplets within a plurality of droplets, changing the desired droplets size (volume) and subsequently sorting the droplets based on their different sizes. The figure shows the system, which includes a detector, a droplet volume controller (e.g., droplet injector) followed by a size sorting device. An optical detector (102) measures or otherwise detects an aspect the droplets prior to injection to determine which drops to increase in size based on a predetermined criteria. Injection of additional fluid and optionally reagents into at least some of the drops can be achieved, for example, by control of a fluid from an injector by electrodes (109, 100), which control release of fluid into the droplets by triggering an electrical field. The drops (some enlarged by injection, some not) then flow into a hydrodynamic size sorter. The sorter includes an intersecting channel used to add continuous phase fluid to the emulsion, to push the drops against one of the walls. This causes the small drops to stream closer to the wall of the channel across from the intersecting channel, and the larger drops, by virtue of their larger size, to stream more centralized compared to the smaller droplets in the channel. In some embodiments, further downstream the channel expands, causing the drops to flow along paths dictated by the average of the streamlines set in motion by the flow from the intersecting channel. Consequently, the small drops will tend to flow farther towards the far edges of the expanded channel, while the large drops flow more centrally. Outlets are placed in these locations to collect the desired drops.

An aspect of the sorter described herein is to change the size of certain droplets within a plurality of droplets and subsequently sort (e.g., passively) the plurality based on droplet size. For example, the droplets are individually flowed through the microfluidic channel by a droplet volume controller (e.g., a droplet injector) and their volume is increased or decreased when an electric field controlled by electrodes (109 and 110), is activated. In some embodiments, an optical measurement by a detector (102) is used to identify desired droplets. The detector can be in communication with the droplet volume controller, thereby controlling which drops' size is altered. The result of this process is a bidisperse collection of drops which can be separated into two distinct streams based on their size. This can be achieved, for example, using a passive hydrodynamic sorting design that sorts the drops based on their size into two different channels.

While the application generally describes controlling the volume and sorting of droplets, it should be appreciated that the methods and systems described herein can equally be applied to any discrete objects that can be injected into or out of. Thus, the methods can be applied, for example, to discrete phases as well as to cells, micelles, liposomes, or other discrete objects or containers that have a boundary, interface, or membrane that prevents or delays entry of external fluid into the object. The methods can be used, for example, to sort cells having a marker of interest (e.g., a marker indicating a disease, e.g. a cancer marker).

Droplets and Microfluidics Systems

In some embodiments, a droplet is formed in a mixture of immiscible fluids (e.g., water and oil). In some embodiments, a droplet is an aqueous droplet that is surrounded by an immiscible carrier fluid (e.g., oil). Methods and compositions for partitioning (e.g., forming droplets from) a sample are described, for example, in published patent applications WO 2010/036352, US 2010/0173394, US 2011/0092373, US 2011/0092376, US2012/0222748; WO2013/09573; and US 2011/0218123 the entire content of each of which is incorporated by reference herein.

In some embodiments, the droplets that are generated are initially (pre-sorting and pre-volume changing) substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns.

In some embodiments, the droplets that are generated are initially (pre-sorting and pre-volume changing) substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. Examples of embodiments in which two or more droplets are fused have been described above. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. Most fluid channels in components of the invention have maximum cross-sectional dimensions less than about 2 mm, and in some cases, less than about 1 mm. In one set of embodiments, all fluid channels containing embodiments of the invention are microfluidic or have a largest cross sectional dimension of no more than about 2 mm or about 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channels) containing embodiments of the invention are less than about 500 microns, less than about 200 microns, less than about 100 microns, less than about 50 microns, or less than about 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5:1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic droplets Encapsulated in Particles Such as Colloidal Particles," published as WO 2006/078841 on Jul. 27, 2006, each incorporated herein by reference in their entireties.

A wide variety of methods and materials exists and will be known and appreciated by one of skill in the art for construction of microfluidic channels and networks thereof, such as those described, for example, in U.S. Pat. No. 8,047,829 and U.S. Patent Application Publication No. 20080014589, each of which is incorporated herein by reference in its entirety. For example, the microfluidic channel may be constructed using simple tubing, but may further involve sealing the surface of one slab comprising open channels to a second flat slab. Materials into which microfluidic channels may be formed include silicon, glass, silicones such as polydimethylsiloxane (PDMS), and plastics such as poly(methyl-methacrylate) (known as PMMA or "acrylic"), cyclic olefin polymer (COP), and cyclic olefin copolymer (COC). The same materials can also be used for the second sealing slab. Compatible combinations of materials for the two slabs depend on the method employed to seal them together. The microfluidic channel may be encased as necessary in an optically clear material to allow for optical excitation (resulting in, e.g., fluorescence) or illumination (resulting in, e.g., selective absorption) of a sample as necessary, and to allow for optical detection of spectroscopic properties of light from a sample, as the sample is flowing through the microfluidic channel. Some examples of such optically clear materials that exhibit high optical clarity and low autofluorescence include, but are not limited to, borosilicate glass (e.g., SCHOTT BOROFLOAT® glass (Schott North America, Elmsford N.Y.)) and cyclo-olefin polymers (COP) (e.g., ZEONOR® (Zeon Chemicals LP, Louisville Ky.)).

Identifying Desired Droplets

A variety of situations can occur in which a mixture of desired and undesired droplets occur in a mixture of droplets. In some embodiments, the desired droplets will contain a reagent, object (e.g., a cell) or molecule that does not occur in the undesired cells. Alternatively, in some embodiments, the desired droplets will lack a reagent, object (e.g., a cell) or molecule that does occur in the undesired cells. In some embodiments, desired droplets will have a small or single cell while undesired cells will have a larger number of cells, or in other embodiments the undesired droplets will not contain cells. In some embodiments, the droplets (desired and undesired) will contain cells but only the desired droplets will contain cells expressing a marker that cells in undesired droplets lack. In some embodiments, the droplets (desired and undesired) will contain cells but only the undesired droplets will contain cells expressing a marker that cells in desired droplets lack.

Methods of detecting desired droplets and distinguishing desired droplets from undesired droplets will depend on the particular criteria for identifying desired droplets. In some embodiments, an optical detector will detect the criteria. In some embodiments, the droplets will contain a delectable label (e.g., a fluorescent label), and in some embodiments the label will be linked to an affinity agent, e.g., an antibody or nucleic acid being complementary to a target. Exemplary optical detectors can include, but are not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays). The optical detector can be in communication (e.g. via wiring or wirelessly) to a mechanism to change volume of targeted droplets.

Changing Volume of the Desired Droplets Relative to Volume of the Undesired Droplets Upon recognition of a desired droplet, a mechanism for changing the droplet volume is activated, thereby increasing or decreasing the volume of the desired droplet. Alternatively, the mechanism for changing the droplet volume can change the volume of undesired droplets. In either case, the result is to change the volume of the desired droplets relative to the undesired droplets, thereby generating a population of desired droplets having a first volume and a population of undesired droplets having a second volume, where the first and second volumes are sufficiently different to passively sort the two populations. It will be appreciated that the first and second volumes will be an average volume within the population, but in general there will be limited variability with in the population. For example, in some embodiments, drop sizes are normally distributed, e.g., with mono-disperse drops being where at least 95% of the measured drops are +/−1 μm of the desired mean value. In some embodiments, the first volume and second volumes differ by at least 5, 10, 15, 20, 25, 50, or 100%, e.g., 5-50%.

In some embodiments, the mechanism (also referred to herein as an "injector") to change volume of targeted droplets comprises an electric field generated by the electrodes (depicted in FIG. 1 as 109, 110) is then switched on and off, to inject or withdraw fluid into or from the droplet, and thereby increase or decrease the droplet size. An example of a droplet injector is described in US Patent Publication No. US2012/0132288. In some embodiments, the flow at the injector is reversed such that a volume of the droplet is removed when the field is turned on, thereby selectively reducing the size of some of the droplets. In any case, the process results in a bi-disperse collection of droplets which is easily separated into two distinct streams.

In some embodiments, instead of injecting additional fluid into target droplets, the target droplets are fused with an adjacent droplet, thereby rendering the target droplet larger.

Passively Sorting Droplets

As described above, the methods described herein involve identification of desired droplets at an upstream location and targeted changing of droplet size such that the droplets can be sorted passively into desired and undesired populations based on volume, size, or other criteria. "Passive sorting" refers to performing sorting by providing a constant force or obstruction that sorts droplets based on their property (e.g., volume, electromagnetic properties, density, etc.) and thus does not involve active detection of the desired criteria at the sorting stage. "Active sorting" on the other hand involves selectively (e.g., on and off depending on the droplet identity) applying a force. For example, "active" sorting of droplets using an electric field might involve a detector that activates the electric field, which is turned on and off in response to the identity of particular droplets. In contrast, passive sorting using an electric field involves the electric field being constantly on. Passive sorting can involve obstructions, hydrodynamic force or other technology, but will always be present and is not varied depending on the identity of the droplets.

Figure 2:
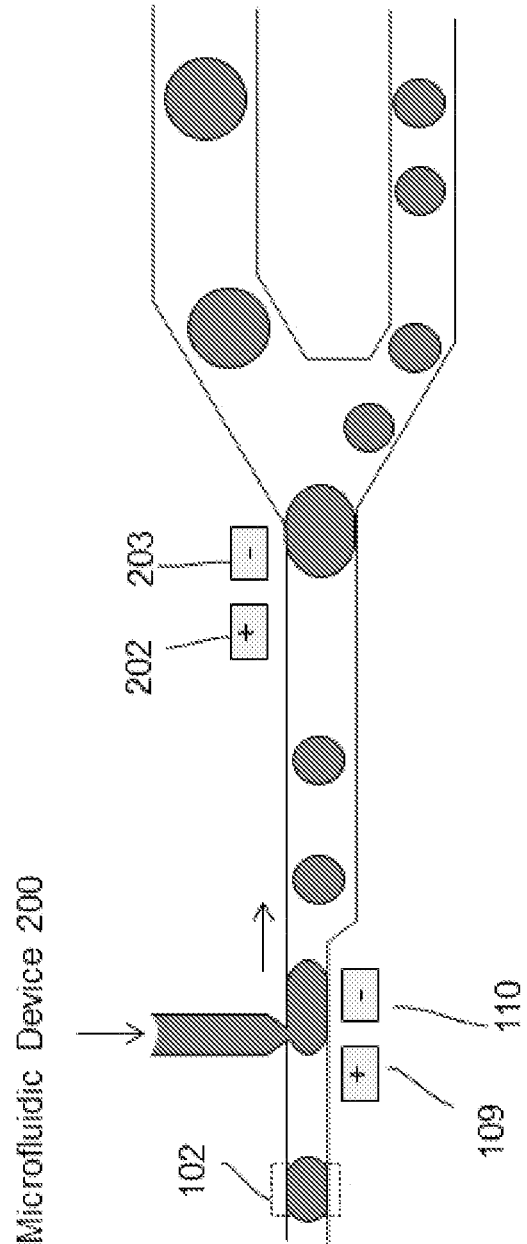
FIG. 2 illustrates another example of droplet size control (e.g., injection) in a drop sorting device. The figures shows an alternate embodiment where the drops are sorted using a fixed electrical field instead of an intersecting channel. As the drops pass electrodes (202, 203) that generate the electric field, the drops are deflected by the field. The deflection of the drops differs for different size drops allowing for them to be guided to different channels.

In some embodiments, the passive sorting comprises a hydrodynamic force, e.g., a constant flow from a side channel such as depicted in FIG. 1. In yet another embodiment, instead of a hydrodynamic force, an electric field is used to force the droplets to one side of the channel. An exemplary embodiment is depicted in FIG. 2. The electric field will generate a force coming from one side of the channel that will have a differentiation effect depending on droplet size, thereby sorting the drops into two distinct streams.

In some embodiments, the injector will further inject one or more substance to assist in later sorting of the droplets. In some embodiments, the injector for changing the volume of the droplets also injects a reagent that changes the electromagnetic properties of the droplet, enhancing the differential effect of the field. In some embodiments, a temperature-sensitive polymer is injected into the desired (or alternatively, the undesired) droplets and the temperature can later be changed to solidify the polymer. For example, molten agarose can be injected. US Patent Application No. 2011/0218123 describes other temperature-sensitive substances that can also be used.

Exemplary passive sorting methods can include any of the following.

Figure 3B:
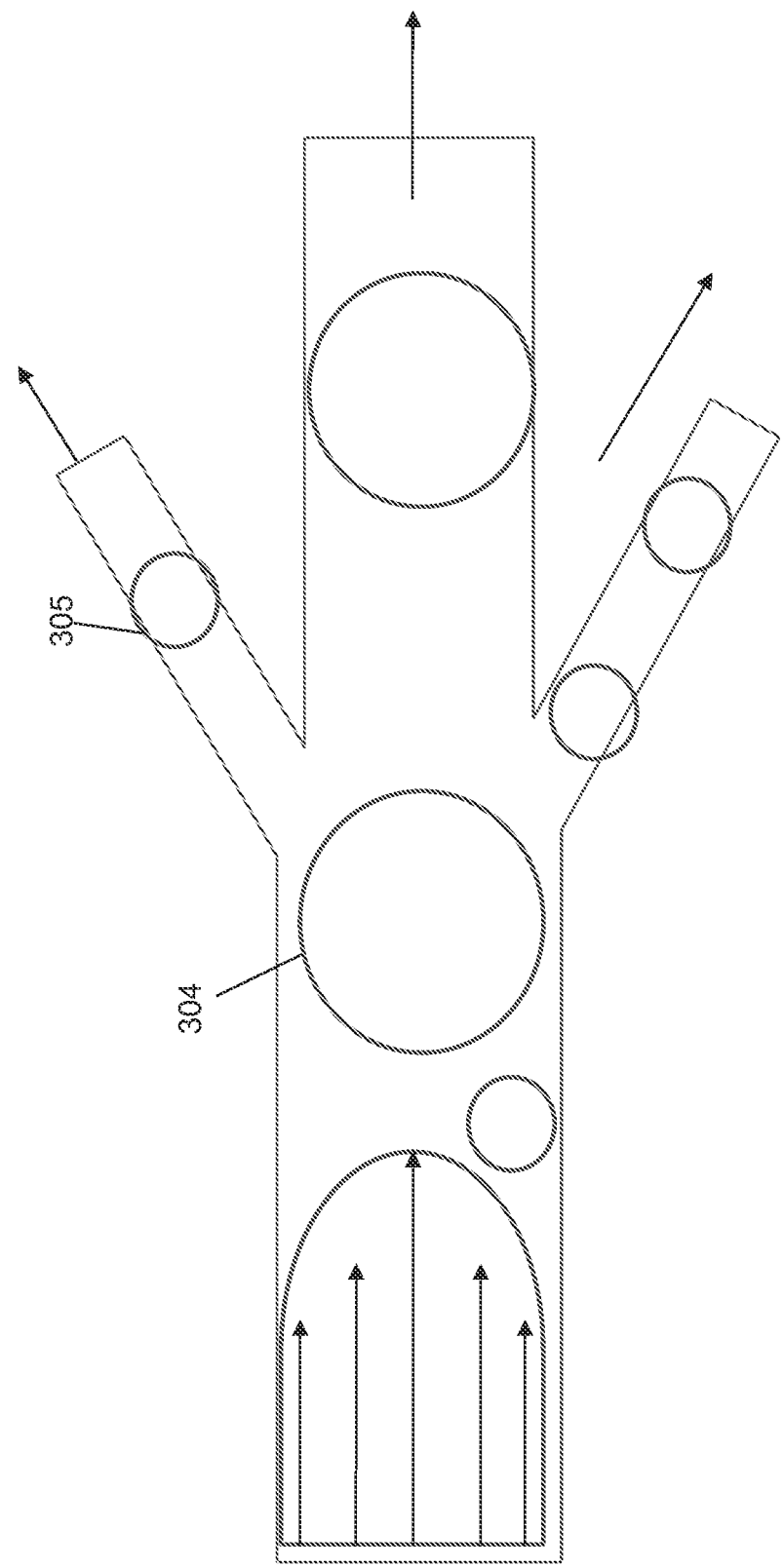
Figure 4A:
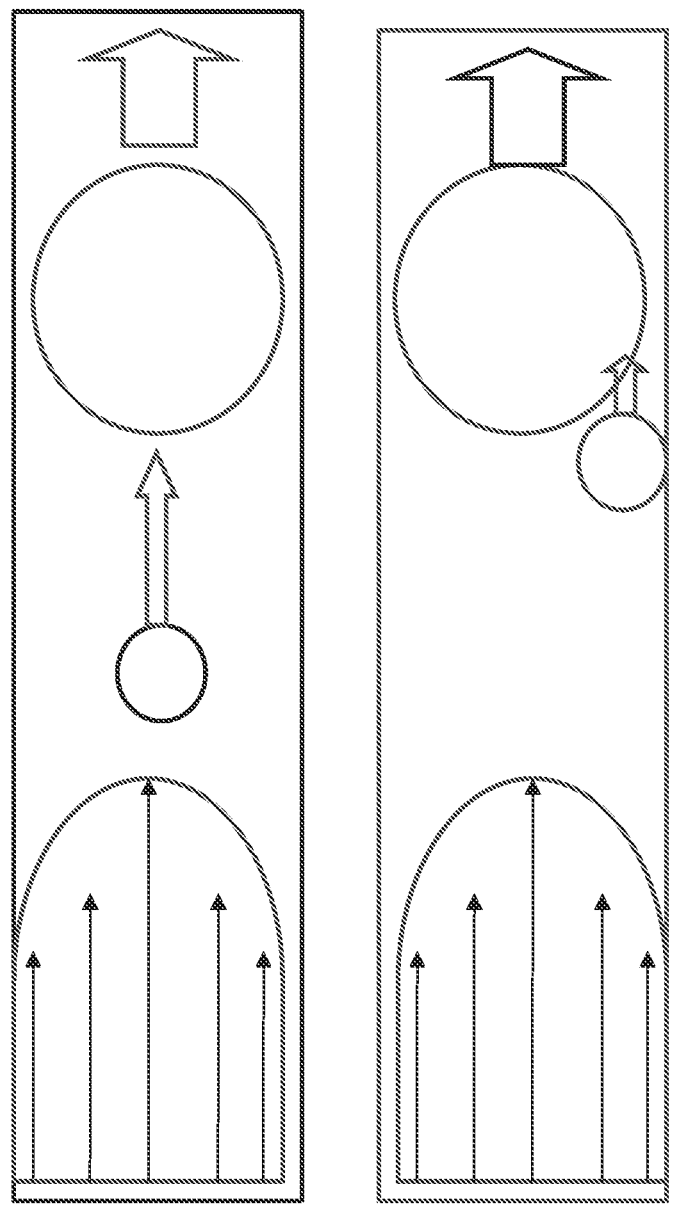
FIG. 4A and 4B illustrate a different passive sorting aspect. Instead of having small side channels to siphon away the drops as depicted in FIG. 3A-B, a rapid expansion in the size of the channel occurs. The fluid flow lines will expand moving left to right in FIG. 4B to fill this new geometry (the profile is still parabolic, but the parabola is now larger). Flow lines in the center of the channel before, will remain near the center of the new expanded channel. However, flow lines near the walls of the old channel will move a larger distance to be next to the wall of the new channel. Small drops which are closer to the walls of the old channel will follow these stream lines and separate from larger drops in the center.
Figure 4B:
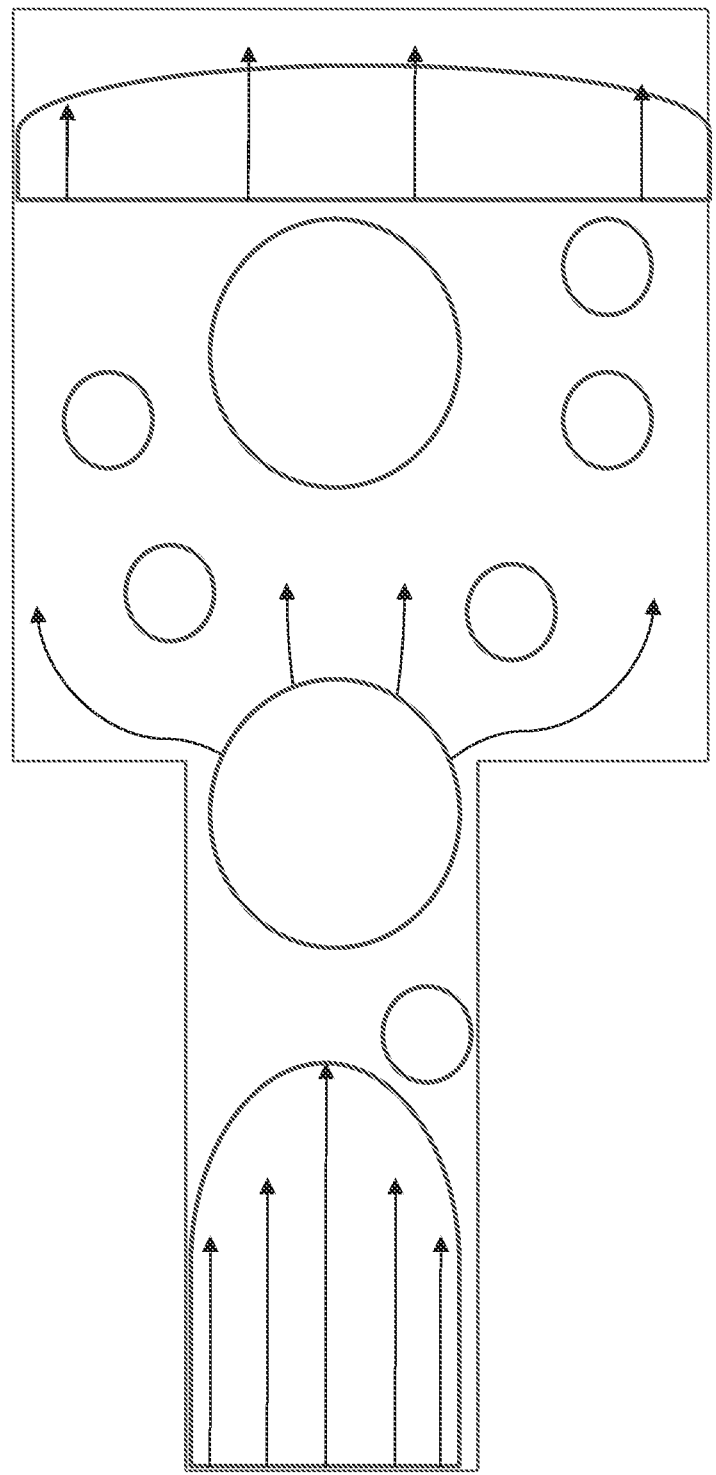

1) Dielectrophoresis (DEP). DEP is a phenomenon in which a force is exerted on a dielectric particle when it is subjected to a non-uniform electric field. Methods of DEP sorting are described in, e.g., Ahn et al., *Applied Physics Letters* 88, 024104 (2006) and Lenshof and Laurell, *Chemical Society Reviews* 39:1203-1217 (2010).
2) Obstacle induced separation. This method is also referred to as deterministic lateral displacement and involves deflecting different sized droplets to a different degree based on the placement of obstacles (posts) in the flow path. Examples of Obstacle induced separation are described in, e.g., Lenshof and Laurell, *Chemical Society Reviews* 39:1203-1217 (2010).
3) Deformability selective separation. This method takes advantage of the differential deformability of different-sized droplets. Examples of deformability selective separation are described in, e.g., Lenshof and Laurell, *Chemical Society Reviews* 39:1203-1217 (2010).
4) Inertial migration. This method relies on inertial forces such as pinching and expanding the channel. Examples of inertial migration are described in, e.g., Karimi, et al., *Biomicrofluidics* 7, 021501 (2013), e.g., FIG. 2. See also, FIG. 3A-B of the present application.
5) Inertial Dean Flows. This method refers to using a curving channels to force larger drops to the side of walls because they respond more to drag forces. Examples of inertial Dean flows are described in, e.g., Karimi, et al., *Biomicrofluidics* 7, 021501 (2013), e.g., FIG. 5.
6) Gravity or centrifugation. In some embodiments, a force (e.g., gravity or force from centrifugation) can be used to separate more dense and less dense droplets.
7) Microfluidic sorting by density. One can flow fluids of different density into a merged channel (two separate channels having fluids of different densities can be merged into one channel). Because in microfluidic flow (low reynolds number, high viscous forces) mixing due to diffusion occurs on a long time scale versus the forward movement of the fluid, when the two fluids come together in the main channel, mixing of the fluid will not occur immediately but will occur over a time period. Drops or particles flowing will have a force applied on them due to the density of the fluid: the parts of the drop in the high density layer will see higher drag forces than the parts of the drop in the lower density layer. Depending on how the density layer in the merged flow is created, drops of different sizes will separate.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method to sort desired droplets from undesired droplets comprising,
    (a) providing a plurality of droplets flowing in a microfluidic channel, wherein the plurality of droplets comprise desired droplets having an optically detectable label and undesired droplets that do not have an optically detectable label,
    (b) identifying desired droplets having an optically detectable label in the plurality of droplets,
    (c) changing volume of the desired droplets by selectively injecting or removing fluid from the desired droplets, changing the volume of the undesired droplets by selectively injecting or removing fluid from the undesired droplets, or a combination thereof such that at least some of the desired droplets have a different volume relative to the undesired droplets,
    (d) passively sorting the desired droplets having the different volume from the undesired droplets, thereby separating the desired droplets from undesired droplets.

2. The method of claim 1, wherein the identifying comprises identifying the desired droplets with an optical detector.

3. The method of claim 1, wherein the changing comprises selectively injecting or removing fluid from the desired droplets.

4. The method of claim 1, wherein a volume controller increases the volume of the desired droplets in response to an electrical field.

5. The method of claim 1, wherein a volume controller decreases the volume of the desired droplets in response to an electrical field.

6. The method of claim 1, wherein the changing comprises selectively injecting or removing fluid from the undesired droplets.

7. The method of claim 6, wherein a volume controller increases the volume of the undesired droplets in response to an electrical field.

8. The method of claim 6, wherein a volume controller decreases the volume of the undesired droplets in response to an electrical field.

9. The method of claim 1, wherein the changing results in at least a majority of the desired droplets in the plurality of droplets having a different volume than the undesired droplets.

10. The method of claim 1, wherein the passively sorting comprises forcing droplets towards a wall of the microfluidic channel, wherein droplets of different sizes are forced a different distance towards the wall.

11. The method of claim 10, wherein the forcing comprises adding a phase fluid continuously to the microfluidic channel through an intersecting channel to push the droplets toward the wall.

12. The method of claim 10, wherein the forcing comprises applying a deflection electrical field to the microfluidic channel to force the droplets towards the wall.

13. The method of claim 1, wherein the changing volume of the desired droplets relative to the volume of the undesired droplets further comprises injecting a reagent that changes the electromagnetic properties of the droplets to increase deflection distance differentiation among the droplets of different volume caused by the deflection electric field.

14. The method of claim 1, wherein the passive sorting is performed by a method selected from the group consisting of dielectrophoresis, obstacle induced separation, deformability selective separation, inertial migration, and inertial Dean flow.

15. A system for sorting droplets, the system comprising:
a source of droplets in fluid communication with a microfluidic channel,
an optical detector positioned for determination of desired droplets in a plurality of droplets in the microfluidic channel,
a droplet volume controller, downstream of the optical detector, configured to change the volume of the desired droplets by selectively injecting or removing fluid from the desired droplets in order to change the volume of the desired droplets relative to the volume of the undesired droplets, and
a droplet size sorter, downstream of the droplet volume controller, in fluid communication with the channel, which separates the desired droplets from undesired droplets.

16. The system of claim 15, wherein the volume controller injects fluid into desired droplets to increase the volume of the droplets.

17. The system of claim 16, wherein the volume controller comprises an electrical field generator such that the volume controller injects fluid into desired droplets in response to an electrical field.

18. The system of claim 15, wherein the volume controller reduces the volume of the desired droplets.

19. The system of claim 18, wherein the volume controller comprises an electrical field generator such that the volume controller reduces the volume of the desired droplets in response to an electrical field.

20. The system of claim 15, wherein the microfluidic channel further comprises an intersecting channel for providing a phase fluid that is added to the microfluidic channel to size-differentially force the droplets toward a wall of the microfluidic channel.

21. The system of claim 15, further comprising one or more electrodes for generating a deflection electrical field applied to the microfluidic channel to deflect the droplets within the microfluidic channel, which results in deflection distances that correspond to the volume of the droplets and allows desired droplets to be separated from the undesired droplets while passing through the size sorter.

22. The system of claim 16, wherein the volume controller additionally injects a reagent that changes the electromagnetic properties of the droplets to increase deflection distance differentiation among the droplets of different volume caused by the deflection electric field.

23. The system of claim 15, wherein the droplet size sorter is selected from the group consisting of a dielectrophoresis droplet size sorter, an obstacle induced separation droplet size sorter, a deformability selective separation droplet size sorter, an inertial migration droplet size sorter, and an inertial Dean flow droplet size sorter.

* * * * *